(12) United States Patent
Ranganathan et al.

(10) Patent No.: US 11,816,608 B2
(45) Date of Patent: Nov. 14, 2023

(54) SYSTEMS AND METHODS FOR SERVICE ALLOCATION BASED ON REAL-TIME SERVICE PROVIDER AND REQUESTOR ATTRIBUTES

(71) Applicant: Verizon Patent and Licensing Inc., Basking Ridge, NJ (US)

(72) Inventors: Prakash Ranganathan, Tamilnadu (IN); Vignesh Sundaram, Erode (IN)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 235 days.

(21) Appl. No.: 17/101,811

(22) Filed: Nov. 23, 2020

(65) Prior Publication Data
US 2022/0164753 A1 May 26, 2022

(51) Int. Cl.
| | | |
|---|---|---|
| *G06Q 10/00* | (2023.01) | |
| *G06Q 10/0631* | (2023.01) | |
| *A61B 5/02* | (2006.01) | |
| *G06V 40/20* | (2022.01) | |
| *G06V 40/16* | (2022.01) | |

(52) U.S. Cl.
CPC ........ *G06Q 10/063112* (2013.01); *A61B 5/02* (2013.01); *G06Q 10/063114* (2013.01); *G06V 40/176* (2022.01); *G06V 40/20* (2022.01)

(58) Field of Classification Search
None
See application file for complete search history.

(56) References Cited

U.S. PATENT DOCUMENTS

| | | | | |
|---|---|---|---|---|
| 9,641,686 | B1* | 5/2017 | Johansson | G06Q 10/06311 |
| 9,648,171 | B1* | 5/2017 | Eftekhari | H04M 3/5232 |
| 10,044,865 | B2* | 8/2018 | Dumaine | H04N 7/147 |
| 10,152,718 | B1* | 12/2018 | Janefalkar | G06F 21/629 |
| 10,523,708 | B1* | 12/2019 | Llincic | H04L 63/0435 |
| 2009/0313049 | A1* | 12/2009 | Joao | G16Z 99/00 |
| | | | | 707/999.009 |
| 2013/0173466 | A1* | 7/2013 | Lepisto | G06Q 20/384 |
| | | | | 705/44 |
| 2017/0148073 | A1* | 5/2017 | Nomula | G06F 16/957 |
| 2017/0273612 | A1* | 9/2017 | Kim | A61B 5/486 |
| 2017/0339276 | A1* | 11/2017 | Eftekhari | G06Q 30/016 |

(Continued)

OTHER PUBLICATIONS

Herzig, Jonathan, et al. "Predicting customer satisfaction in customer support conversations in social media using affective features." Proceedings of the 2016 Conference on User Modeling Adaptation and Personalization. 2016. (Year: 2016).*

(Continued)

*Primary Examiner* — Gurkanwaljit Singh

(57) ABSTRACT

A system described herein may provide a technique for identifying states associated with service providers based on biometric, sensor, and/or other information associated with a set of service providers. A request for service may be received, and a particular service provider may be selected based on a particular state associated with the particular service provider, as determined based on the biometric, sensor, and/or other information associated with the particular service provider. State information associated with a requestor of the service may be identified and used as a factor in selecting the particular service provider to respond to the service request.

20 Claims, 10 Drawing Sheets

(56) References Cited

U.S. PATENT DOCUMENTS

| | | | | |
|---|---|---|---|---|
| 2017/0353605 | A1* | 12/2017 | Dumaine | G06K 9/6267 |
| 2018/0032944 | A1* | 2/2018 | Sarvana | G06Q 10/063114 |
| 2018/0110460 | A1* | 4/2018 | Danson | A61B 5/14542 |
| 2018/0114111 | A1* | 4/2018 | Gill | G06N 5/022 |
| 2018/0285879 | A1* | 10/2018 | Gadnis | H04L 9/0825 |
| 2020/0000337 | A1* | 1/2020 | Ducao | G16H 40/67 |
| 2020/0218767 | A1* | 7/2020 | Ritchey | G09G 5/14 |
| 2020/0304542 | A1* | 9/2020 | Ilincic | H04M 3/5175 |

OTHER PUBLICATIONS

Yu, Han, et al. "A survey of multi-agent trust management systems." IEEE Access 1 (2013): 35-50. (Year: 2013).*

Doucet, Lorna. "Responsiveness: emotion and information dynamics in service interactions." (1998). (Year: 1998).*

Galitsky, Boris, Josep-Lluis de la Rosa, and Boris Kovalerchuk. "Discovering common outcomes of agents' communicative actions in various domains." Knowledge-Based Systems 24.2 (2011): 210-229. (Year: 2011).*

Thomas, Kavitha P., and A. P. Vinod. "Toward EEG-based biometric systems: The great potential of brain-wave-based biometrics." IEEE Systems, Man, and Cybernetics Magazine 3.4 (2017): 6-15. (Year: 2017).*

Ohme, Ratal, Michal Matukin, and Beata Pacula-Lesniak. "Biometric measures for interactive advertising research." Journal of interactive advertising 11.2 (2011): 60-72. (Year: 2011).*

* cited by examiner

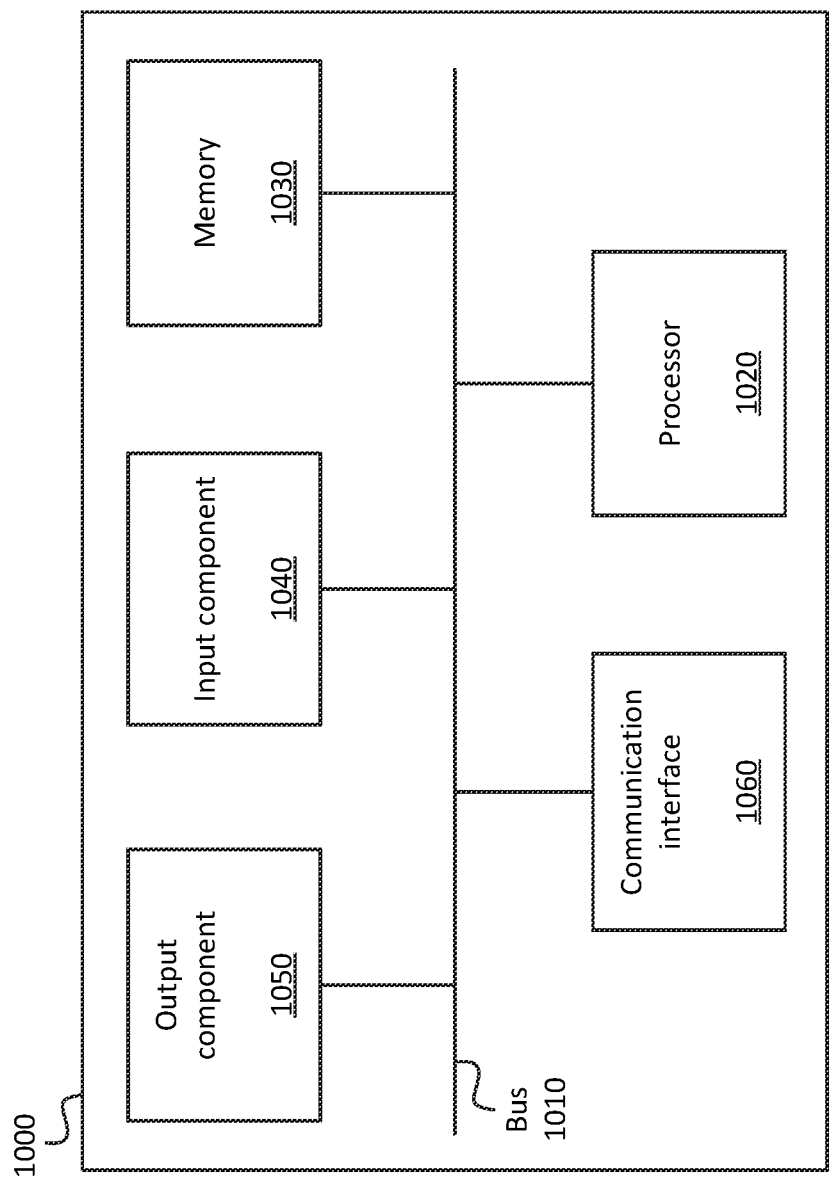

SYSTEMS AND METHODS FOR SERVICE ALLOCATION BASED ON REAL-TIME SERVICE PROVIDER AND REQUESTOR ATTRIBUTES

BACKGROUND

Service providers may provide services to requestors, such as technical support services, providing product information, responding to inquiries, and/or other services. Such services may be provided via voice communications such as telephone calls, written chat communications, or the like.

BRIEF DESCRIPTION OF THE DRAWINGS

FIG. 10 illustrates example components of one or more devices, in accordance with one or more embodiments described herein.

DETAILED DESCRIPTION OF EXAMPLE EMBODIMENTS

Figure 1:
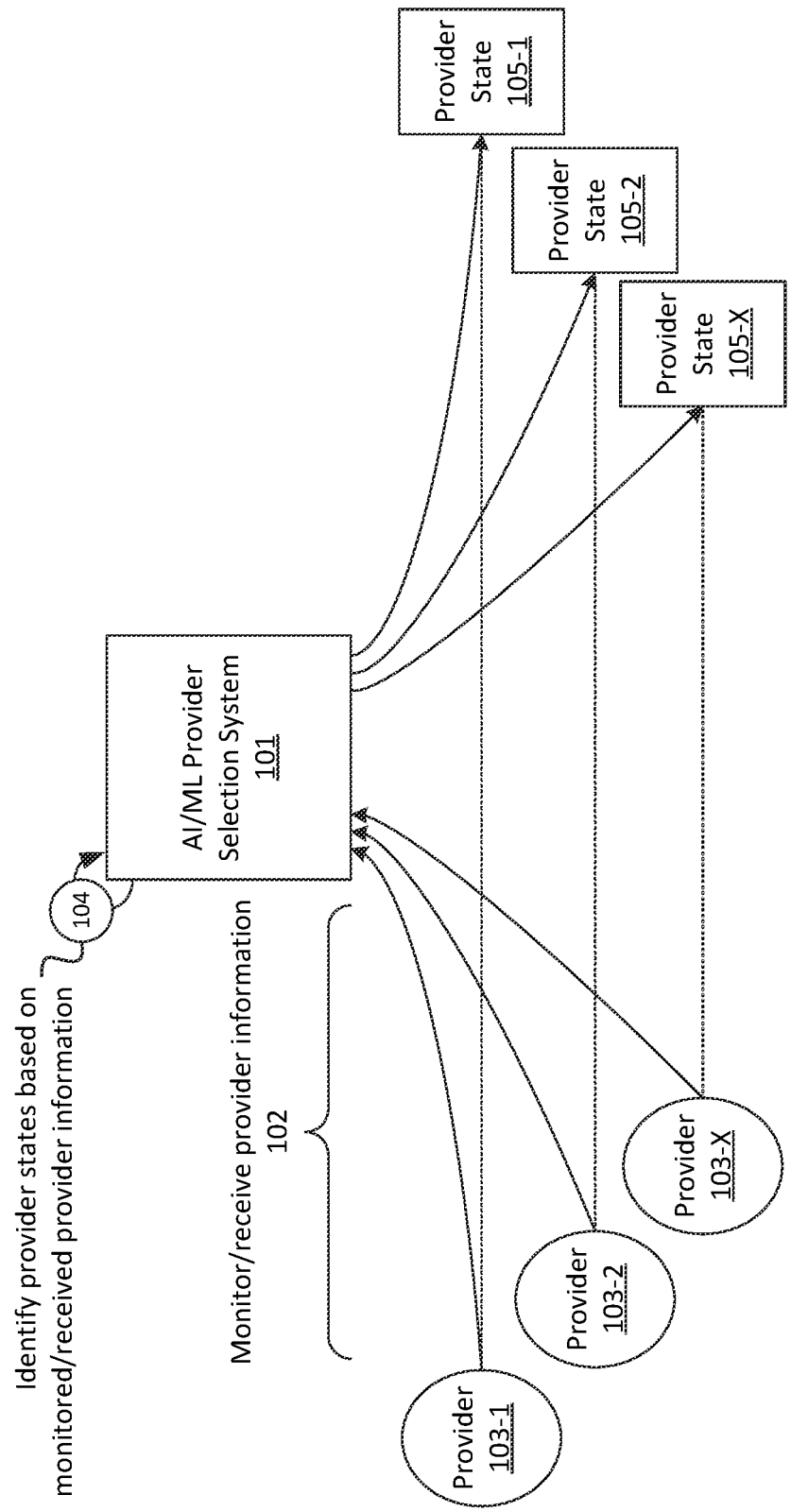
FIG. 1 illustrates an example determination of respective states of a set of service providers (referred to herein as "providers") based on information associated with the providers, in accordance with some embodiments.

The following detailed description refers to the accompanying drawings. The same reference numbers in different drawings may identify the same or similar elements.

Embodiments described herein provide for the use of artificial intelligence/machine learning ("AI/ML") techniques or other suitable techniques to assign service providers (referred to herein simply as "providers") to handle requests from service requestors (referred to herein as "requestors"). A "provider," as referred to herein, may include any type of provider of a suitable type of requested service. For example, providers may include service representatives, operators, and/or other types of providers that handle support requests, information requests, and/or requests for other types of service from a requestor. In some embodiments, such providers may be associated with a call center or other facility that provides services via voice communications (e.g., telephone calls or other types of voice calls), video communications (e.g., video calls, videoconferences, etc.), text-based communications, or other types of communications. Similarly, a requestor may request service from the provider by placing a request via a telephone call, a web page, a web portal, an application (or "app"), and/or in some other suitable manner.

In accordance with embodiments described herein, requests may be provided to an appropriate provider, out of a set of candidate providers, based on information associated with the candidate providers, the requestor, the requested service, and/or other factors. As described herein, provider information (e.g., based on which an appropriate provider may be selected) for a given provider may include biometric, vital, and/or sensor information related to the provider, such as brain wave information, speech patterns, pulse (e.g., heart rate), blood pressure, temperature, a measure of caloric burn and/or metabolic rate, sleep patterns, facial expressions, and/or other suitable types of information. Such provider information may be monitored and/or collected by wearable devices or sensors worn by a given provider, such as "smart" headphones, "smart" glasses, a "smart" watch, a fitness tracker, one or more medical devices or sensors, or other apparatus that is capable of collecting one or more of the above-mentioned types of information. In some embodiments, provider information may be monitored and/or collected by another type of device or system, such as a microphone, a camera, a smartphone, and/or some other type of device or system that includes sensors and/or other suitable functionality to determine such information. Further, requestor information (e.g., based on which an appropriate provider may be selected) for a given requestor may include request type (e.g., a type or amount of service being requested), request frequency (e.g., how often the given requestor requests service), speech patterns, text-based communication patterns, and/or other information associated with the requestor.

Generally, for example, provider information may be used to determine a state associated with a given provider, which may indicate the provider's effectiveness when handling particular types of requests and/or particular requestors at a particular time. For example, based on a given provider's brain wave information (e.g., based on alpha, beta, gamma, delta, and/or theta waves), sleep patterns, blood pressure, and speech patterns, a system of some embodiments may determine that the provider is in an alert and/or anxious state, and may avoid selecting this provider for service request with a relatively difficult to handle service type and/or a requestor whose speaking patterns indicate that the requestor may be upset or angry. Instead, the given provider may be matched with another, less stress-inducing service request, and/or the given provider may be instructed to rest, take a break, end his or her shift, or the like. For example, in some embodiments, remedial actions such as notifying the provider to rest, take a break, etc. may be identified based on a determined provider state, without consideration to requests or requestors. Accordingly, provider productivity and/or performance may be enhanced. Similarly, in embodiments where providers are matched to requests from requestors, the user experience for requestors may be enhanced by virtue of determining a provider whose state is best suited for a particular request or requestor state.

As shown in FIG. 1, for example, AI/ML Provider Selection System ("APSS") 101 may monitor and/or receive (at 102) provider information associated with a set of providers 103-1 through 103-X (sometimes referred to individually herein as "provider 103" or collectively as "providers 103"). For example, as similarly discussed above, such provider information may include biometric information, sensor information, or the like associated with each respective provider 103. For example, provider 103-1 may be associated with a first "smart" headset that measures brain wave activity associated with provider 103-1, while provider 103-2 may be associated with a second "smart" headset that measures brain wave activity associated with provider 103-2. As another example, APSS 101 may receive video information depicting provider 103-1, provider 103-2, and/or provider 103-X, and may perform a suitable visual analysis (e.g., computer vision analysis, pattern matching analysis, and/or other suitable image or visual analysis) to determine facial expressions associated with provider 103-1, provider 103-2, and provider 103-X.

As further shown, APSS 101 may identify (at 104) a respective provider state 105 for each provider 103. For example, APSS 101 may determine that provider 103-1 is associated with provider state 105-1, that provider 103-2 is associated with provider state 105-2, and that provider 103-X is associated with provider state 105-X. Thus, as further described below, the identification of a respective provider state 105 for a given provider 103 may be based on analyzing some or all of the received (at 102) provider information, and comparing the provider information to one or more models.

While the figure depicts provider information as being monitored and/or received "from" respective providers 103, in practice, APSS 101 may receive such information from devices or systems not explicitly shown in FIG. 1. For example, APSS 101 may receive provider information from a User Equipment ("UE") such as a mobile telephone, an Internet of Things ("IoT") device, a workstation, a tablet computer, a web server, and/or some other type of device or system. Such UE or other device may include and/or may be communicatively coupled to one or more sensors (e.g., brain wave sensors, heartbeat monitors, blood pressure monitors, etc.) or other suitable types of devices or components that are capable of capturing or otherwise determining provider information discussed herein.

Figure 2:
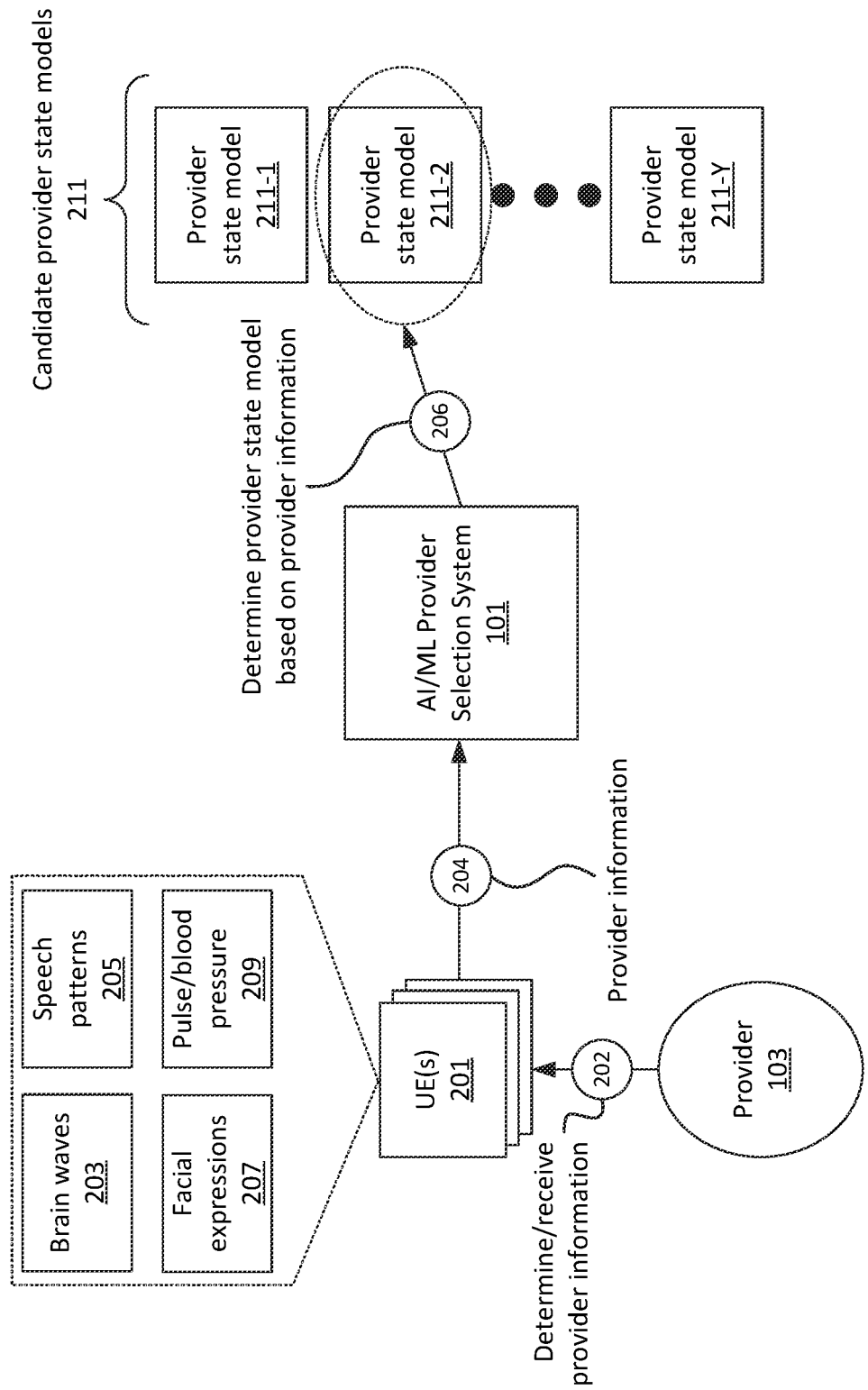
FIG. 2 illustrates an example determination of a particular state associated with a particular provider based on comparing provider information associated with the particular provider to a set of candidate provider state models, in accordance with some embodiments.

For example, as shown in FIG. 2, one or more UEs 201 may determine and/or receive (at 202) biometric information, sensor information, and/or information associated with provider 103. While the example of FIG. 2 is shown in the context of such information being determined or received from one or more UEs 201, in practice, some embodiments may determine and/or receive such information from one or more other types of devices or systems. Further, while FIG. 2 is shown in the context of one or more UEs 201 (denoted in the figure as "UE(s) 201"), the description below provided examples in the context of one UE 201 for the sake of clarity. Additionally, as noted above, UEs 201 may include and/or may be communicatively coupled to one or more sensors or other types of components that are capable of generating, receiving, determining, etc. the types of provider information described herein.

As shown, UE 201 may determine and/or receive brain wave information 203, speech pattern information 205, facial expression information 207, and pulse and/or blood pressure information 209. In practice, UE 201 may determine and/or receive other suitable types of information in addition to, or in lieu of, brain wave information 203, speech pattern information 205, facial expression information 207, and pulse and/or blood pressure information 209. For example, UE 201 may include and/or may be communicatively coupled to an Electroencephalography ("EEG") device or other suitable device that is capable of detecting brain wave information 203 associated with a given user (e.g., provider 103). In some embodiments, UE 201 may include and/or may be communicatively coupled to a wearable "smart" device, such as a set of "smart" headphones, "smart" glasses, or the like, that include an EEG device or other suitable device or sensor. Generally, brain waves may be measurable in different frequencies or bands, sometimes referred to as alpha, beta, gamma, delta, and theta. Different measurements (e.g., amplitudes) across these varying frequencies or bands may correspond to levels of happiness, stress, anger, frustration, or other emotions or moods of a user.

Speech pattern information 205 may include the content of speech and/or text-based communications from provider 103 (e.g., via UE 201, such as through a voice- or video-based call or a text-based messaging communication), which may include a transcribed version of speech from provider 103. For example, UE 201 and/or APSS 101 may use speech-to-text techniques in order to generate or determine speech pattern information 205. Additionally, or alternatively, speech pattern information 205 may be based on the tone, volume, pitch, and/or other audible features (e.g., non-verbal features) of speech from provider 103 (e.g., via UE 201). For example, generally, relatively loud (e.g., having a decibel rating or other measure of loudness above a threshold) utterances from provider 103 may indicate that provider 103 is upset or frustrated, while utterances that are within or "normal" range of volume associated with provider 103 may indicate that provider 103 is not upset or frustrated, or that provider 103 is content or happy. As another example, relatively fast (e.g., greater than a threshold quantity of words per second, minute, etc.) speech may indicate that provider 103 is excited, relatively slow speech may indicate that provider 103 is tired or confused, and speech within a "normal" or average range associated with provider 103 may indicate that provider 103 is not excited, tired, or confused. In some embodiments, UE 201 may include, and/or may be communicatively coupled to, a microphone or other device that is capable of capturing audible and/or written speech from provider 103.

Facial expression information 207 may include images or video of a face of provider 103. For example, UE 201 may include and/or may be communicatively coupled to a camera or other device that is capable of capturing images and/or video associated with provider 103. For example, such camera may be situated or affixed at a workstation associated with provider 103. Generally, when facial expression information 207 includes images or video that depict a scowling face of provider 103, facial expression information 207 may indicate that provider 103 is upset or angry. As another example, when facial expression information 207 includes images or video that depict a smiling face of provider 103, facial expression information 207 may indicate that provider 103 is happy. As discussed above, facial expression information 207 may be determined via computer vision analysis, pattern matching analysis, AI-based imagine analysis, and/or other suitable image or visual analysis).

Pulse and/or blood pressure information 209 may include data (e.g., time-keyed data points, graphs, or other suitable representation) of a pulse, blood pressure, or other vital data associated with provider 103. For example, UE 101 may include, or may be communicatively coupled, an electrocardiogram ("ECG"), a blood pressure monitor, a blood oxygen sensor, or other suitable device, sensor, component, etc. that collects and/or measures vital information associated with provider 103.

Although example types of information (e.g., biometric and/or sensor information) associated with provider 103, are discussed above, in practice, other types of biometric and/or sensor information may be used in the manner described herein. For example, sleep patterns associated with particular providers may be determined by UEs associated with respective providers, such as mobile telephones, fitness trackers, or other suitable devices or systems. Sleep patterns may include, for example, duration of sleep, amount of movement while sleeping, breathing patterns while sleeping, and/or other suitable information. Further, while example types of sensors are discussed above, in practice, other types of sensors, components, devices, etc. may be used to determine or generate provider information.

UE 201 may output (at 204) provider information to APSS 101. For example, UE 201 may communicate with APSS 101 via an application programming interface ("API"), a web portal, or some other suitable communication pathway. UE 201 may output the provider information on an ongoing basis, such as a periodic or intermittent basis, such that APSS 101 is able to monitor (e.g., at 102) provider information on an ongoing basis and determine (at 206) provider state information for each provider 103 based on up-to-date information. For example, as the mood or effectiveness of provider 103 changes, some or all of the monitored provider information (e.g., brain wave information 203, speech pattern information 205, etc.) may change, and the corresponding provider state model 211 may change. For example, in the example of FIG. 2, APSS 101 may determine (at 206) that provider 103 is associated with particular provider state model 211-2 (e.g., may select provider state model 211-2 out of a set of candidate provider state models 211) based on the provider information over a given time period. During another time period, APSS 101 may receive a different set of provider information (e.g., different sensor readings, biometric information, etc.) for provider 103 and may determine based on such changed information that provider 103 is associated with a different provider state model 211. For example, one provider state model 211 may relate to a "happy" state, another provider state model 211 may relate to a "tired" state, etc. As such, the respective provider state model 211 for a given provider 103 may change over time, as the provider's mood and/or other attributes change.

In order to determine a particular provider state model 211 for provider 103 based on the received provider information, APSS 101 may use AI/ML techniques (e.g., K-means clustering, neural networks, reinforced and/or unreinforced learning, and/or other AI/ML techniques) to correlate provider information to a particular provider state model 211. Generally, in the example of FIG. 2, brain wave information 203 associated with provider 103 may match (e.g., may exactly match, may have at least a threshold measure of similarity, etc.) brain wave information associated with provider state model 211-2. As another example, again in the context of FIG. 2, speech pattern information 205 associated with provider 103 may match speech pattern information associated with provider state model 211-2, and/or may more closely match the speech pattern information associated with provider state model 211-2 than speech pattern information associated with provider state model 211-1 or provider state model 211-Y.

In some embodiments, a "match" may refer to an exact matching between monitored provider information and information associated with a given model. Additionally, or alternatively, a "match" may refer to a suitable measure of similarity (e.g., using a similarity or correlation analysis) between some or all of the monitored provider information and information associated with a given model.

While the selection (at 206) of a particular provider state model 211-2 for provider 103 is described as being based on provider information (e.g., brain wave information 203, speech pattern information 205, facial expression information 207, pulse and/or blood pressure information 209, and/or other biometric and/or sensor information), in practice, APSS 101 may select a particular provider state model 211 for provider 103 based on one or more other types of information. For example, APSS 101 may make such selection based on factors such as how long provider 103 has been providing service before a given request for service is received (e.g., if provider 103 has been working a relatively long shift), a level of experience or expertise of provider 103 in a given field or specialty (e.g., as such field or specialty relates to the request), a history of the provider 103 with a particular requestor (e.g., which may indicate that provider 103 and the particular requestor have interacted in the past), and/or other factors.

In addition to identifying provider states (e.g., as discussed above with respect to FIGS. 1 and 2), APSS 101 may identify requestor states. As discussed below, APSS 101 may select a particular provider 103 to handle a service request from a given requestor 303 based on identified provider and requestor states, in order to maintain or enhance the user experience for both providers 103 and requestors 303.

Figure 3:
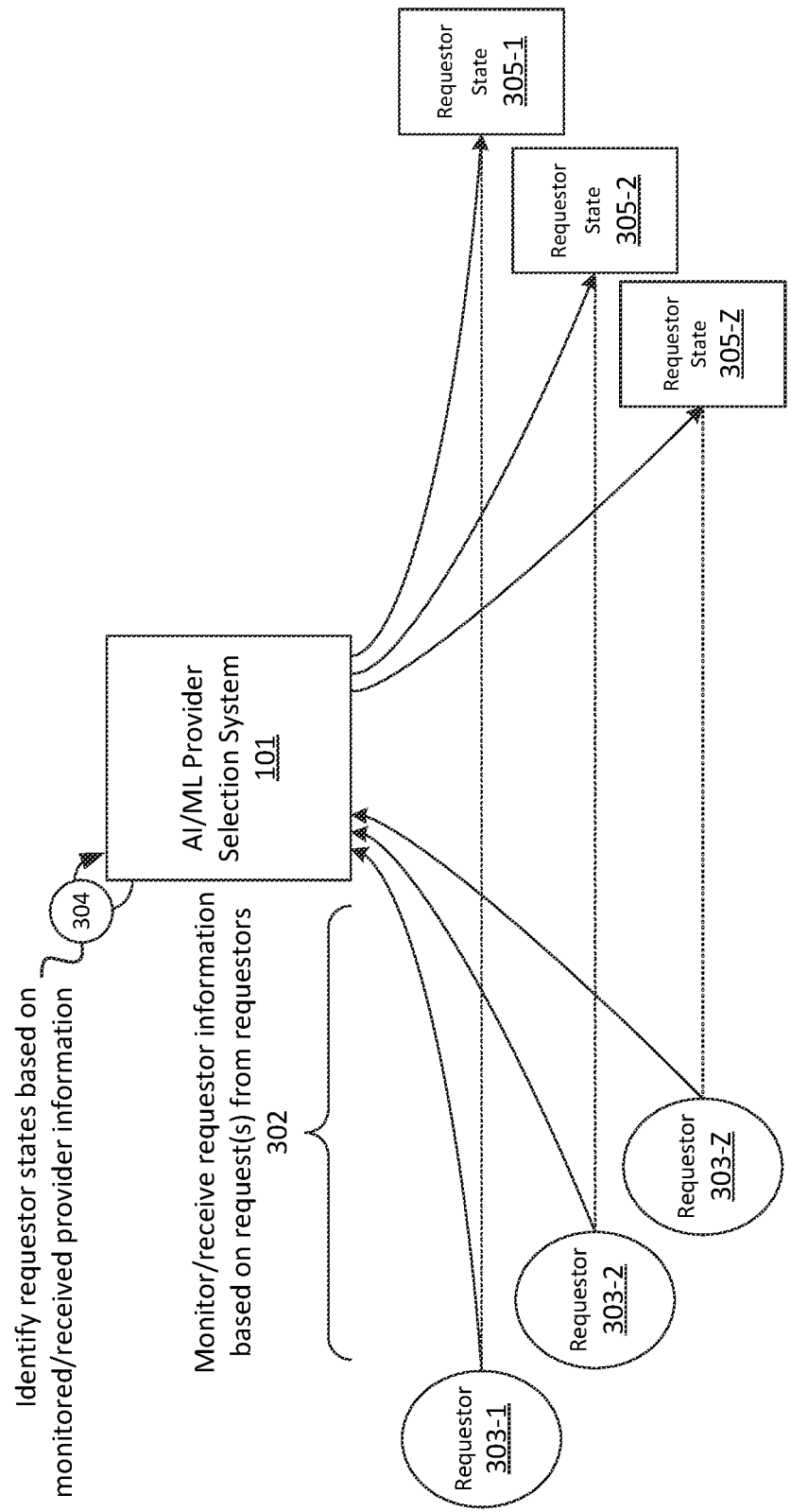
FIG. 3 illustrates an example determination of respective states of a set of service requestors (referred to herein as "requestors") based on information associated with the requestors, in accordance with some embodiments.

As shown in FIG. 3, for example, APSS 101 may monitor and/or receive (at 302) requestor information associated with one or more requestors who have requested a service. In some embodiments, such requests may include contacting a call center, support messaging system, and/or other device or system for which services are provided by providers 103. As similarly described above with respect to providers 103, and as discussed in more detail below, APSS 101 may identify (at 304) respective requestor states associated with requestors 303. For example, APSS 101 may determine that requestor 303-1 is associated with requestor state 305-1, requestor 303-2 is associated with requestor state 305-2, and requestor 303-Z is associated with requestor state 305-Z.

Figure 4:
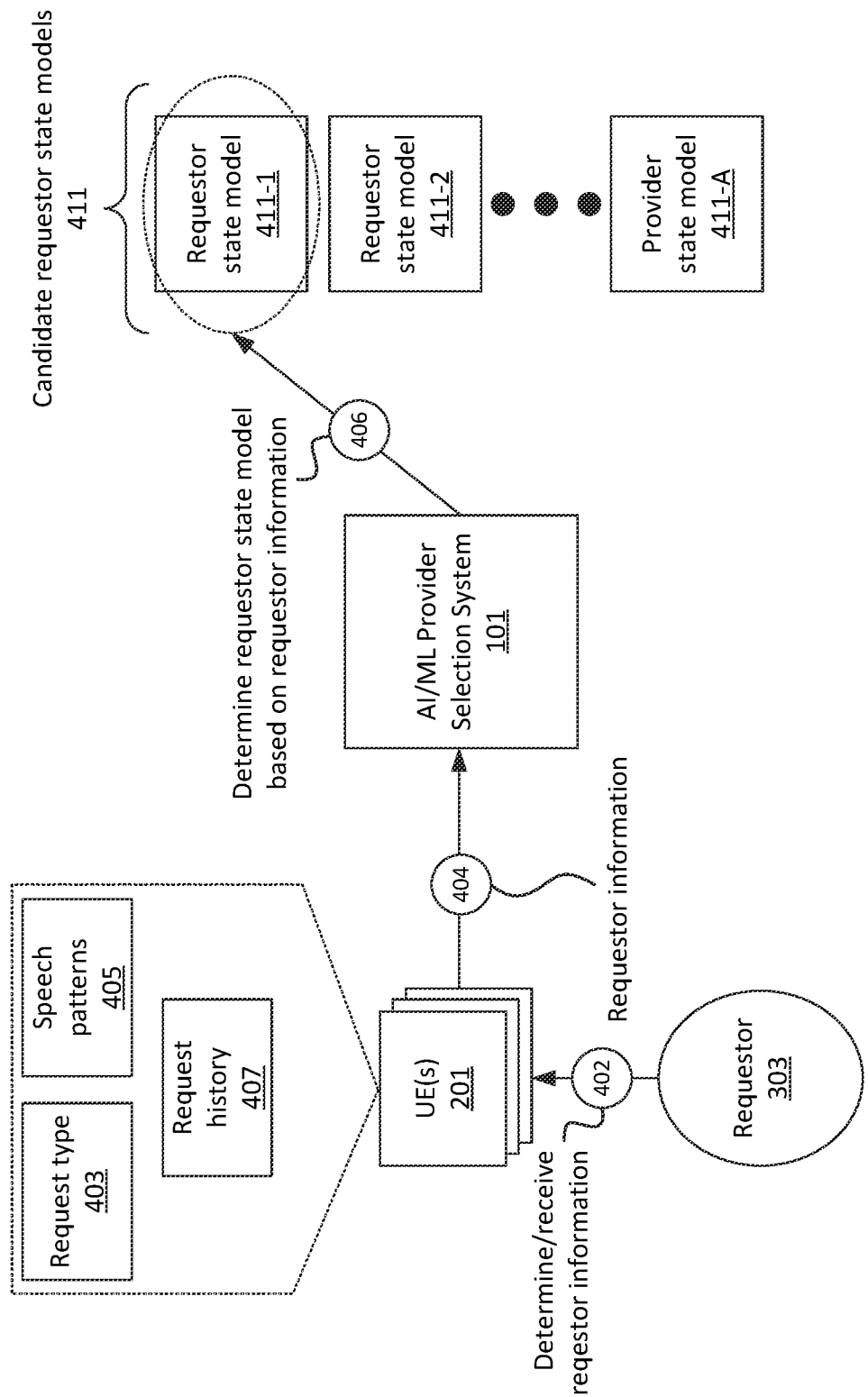
FIG. 4 illustrates an example determination of a particular state associated with a particular requestor based on comparing provider information associated with the particular requestor to a set of candidate requestor state models, in accordance with some embodiments.

As shown in FIG. 4, for example, one or more UEs 201 may determine and/or otherwise receive (at 402) requestor information associated with requestor 303. Additionally, or alternatively, APSS 101 may determine requestor information based on information provided by UE 201, requestor 303, and/or some other source. Requestor information may include, for example, request type information 403, speech pattern information 405, and request history information 407 and/or one or more other types of information in addition to, or in lieu of, request type information 403, speech pattern information 405, and request history information 407.

While the same reference numeral (i.e., 201) is used in FIGS. 2 and 4 for UEs, the UE(s) 201 of FIG. 4 may be a different UE or set of UEs than the UE(s) of FIG. 2. For example, UEs 201 of FIG. 4 may be different types of UEs, and/or may be different instances of the same type of UE as UEs 201 of FIG. 2.

Request type information 403 may indicate a type of request or service. For example, request type information 403 may indicate that requestor 303 is requesting technical support with a particular device (e.g., a particular make or model of telephone, television, laptop computer, or other type of device), may indicate that requestor 303 has an inquiry regarding upgrading a level of service (e.g., Internet service, wireless telephone service, etc.), or some other type of service. Such request types 403 may correspond to, for example, specialties or skills with which one or more providers 103 are associated. For example, one particular provider 103 may be associated with a "mobile telephone technical support" skill, while another particular provider may be associated with a "television technical support" skill.

Speech pattern information 405 may include information similar to that described above with respect to 205. For example, speech pattern information 405 may include the content and/or audible attributes (e.g., tone, pitch, volume, etc.) of speech or text-based communications from requestor 303 (e.g., via UE 201).

Request history information 407 may include information regarding past service requests associated with requestor 303. For example, request history information 407 may indicate a time at which one or more previous service requests were received from requestor 303 (e.g., via UE 201 and/or some other device or system), one or more types of service previously requested, and/or other history information associated with requestor 303. Such information may indicate, for example, whether requestor 303 is making repeat requests for the same type of service, which may indicate a level of dissatisfaction, frustration, or the like.

APSS 101 may receive (at 404) the requestor information from UE 201 and/or some other devices or systems. In some embodiments, APSS 101 may receive the requestor information in conjunction with a request for service from requestor 303. In some embodiments, APSS 101 may receive the requestor information on some other basis, such as an ongoing, periodic, and/or intermittent basis.

APSS 101 may further determine (at 406) a particular requestor state model 411 associated with requestor 303. For example, APSS 101 may select requestor state model 411-1 out of a set of requestor state models 411 based on matching, correlating, etc. the requestor information to attributes or information associated with requestor state model 411-1. For example, as similarly noted above, APSS 101 may perform a similarity analysis or other suitable technique to determine which requestor state model 411 matches the requestor information, and/or which particular requestor state model 411 of the candidate set of requestor state models 411 matches the requestor information.

As similarly noted above, APSS 101 may determine (at 406) a matching requestor state model 411 for requestor 303 in a dynamic fashion, such that the same requestor 303 may be associated with different requestor state models 411 at different times. For example, requestor 303 may be associated with a first requestor state model 411 when issuing a first service request, and may be associated with a different second requestor state model 411 when issuing a second service request. For example, requestor 303 may initially request technical support for a particular model of smart phone, at which point APSS 101 may determine that requestor 303 is associated with a "mild" or "happy" state (e.g., associated with a first requestor state model 411). Requestor 303 may later request technical support for the same smart phone (e.g., a subsequent service request of the same type), and APSS 101 may further receive information indicating that requestor 303 is associated with particular speech pattern information 405, indicating louder and/or faster speech patterns. Based on receiving this second request, APSS 101 may determine that requestor 303 is associated with a "frustrated" or "angry" state (e.g., associated with a different second requestor state model 411).

Figure 5:
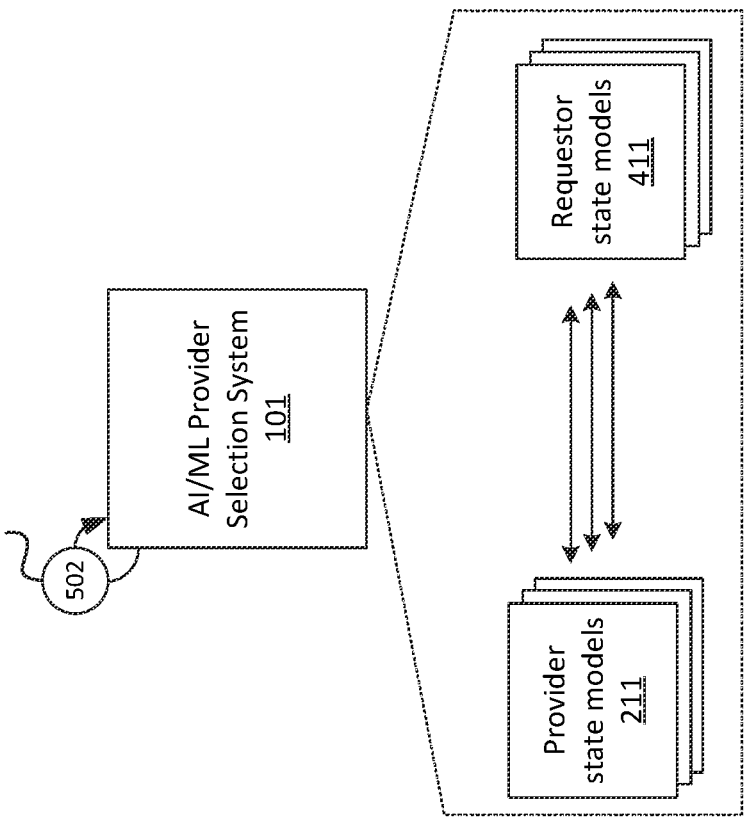
FIG. 5 illustrates an example correlation between respective provider state models and requestor state models, in accordance with some embodiments.

As shown in FIG. 5, APSS 101 may further determine (at 502) correlations between provider state models 211 and requestor state models 411. The correlation may include generating or determining affinities, scores, and/or other parameters or characteristics that indicate that a particular provider state model 211 and a particular requestor state model 411, and/or that indicate how strongly or closely provider state model 211 and requestor state model 411 are correlated. For example, APSS 101 may determine (at 502) that provider state model 211-1 is relatively closely correlated to requestor state model 411-1 (e.g., a correlation score of 99 on a scale of 1 to 100), that provider state model 211-1 is less strongly correlated to requestor state model 411-2 (e.g., a correlation score of 50 on a scale of 1 to 100), and that provider state model 211-1 is not strongly correlated to, or is not at all correlated to, requestor state model 411-3 (e.g., a correlation score of 1 on a scale of 1 to 100).

As discussed herein, when receiving a request from a particular requestor 303, APSS 101 may determine (e.g., at 406) a particular requestor state model 411 associated with requestor 303, and/or associated with the request from requestor 303. APSS 101 may further identify a particular provider 103 to provide the requested service based on respective provider state models 211 associated with a set of candidate providers 103 (e.g., determined at 206). Specifically, for example, APSS 101 may identify an appropriate provider 103 based on correlating provider state models 211, associated with the candidate set of providers 103, to the particular requestor state model 411 identified with respect to requestor 303. For example, APSS 101 may select a particular provider 103 which is associated with the particular provider state model 211 that has a highest measure of correlation to requestor state model 411 associated with requestor 303.

In some embodiments, APSS 101 may utilize one or more other factors in selecting provider 103 to service the request from requestor 303 (e.g., in addition to the correlation between provider state model 211 and requestor state model 411). For example, in some embodiments, such factors may result in APSS 101 selecting a particular provider 103 which is associated with a provider state model 211 that has a lower measure correlation to requestor state model 411 than the highest correlation between provider state models 211 of candidate providers 103 and requestor state model 411. For example, such factors may include a service history between a particular provider 103 and a particular requestor 303. For example, if requestor 303 has expressed dissatisfaction with services received from the particular provider 103 and/or an interaction with provider 103, APSS 101 may select a different provider 103 to provide service in response to a service request from requestor 303, even if a provider state model 211 associated with the particular provider 103 has a highest measure of correlation to requestor state model 411 associated with requestor 303. As another example, requestor 303 may indicate a language preference that does not fall within a set of languages associated with (e.g., spoken by) provider 103, and APSS 101 may select a provider 103 based on language preference and based on correlating requestor state model 411 to a particular provider state model 211 associated with the selected provider 103.

In some embodiments, APSS 101 may utilize one or more AI/ML techniques to generate or refine the correlations between provider state models 211 and requestor state models 411. In some embodiments, APSS 101 may receive a set of "training data" that indicates an initial set of correlations between one or more provider state models 211 and one or more requestor state models 411, may execute simulated interactions between providers 103 (associated with provider state models 211) and requestors 303 (associated with requestor state models 411), and may use feedback from the simulated interactions to modify measures of correlations between respective provider state models 211 and requestor state models 411. For example, such feedback may include quantitative feedback such as elapsed time to resolve a particular request, such as a duration of a telephone call, a duration of a text-based communication session, a time elapsed between the service request and a determination that a particular device or system that is the subject of the request is operating within a set of operational parameters, or other quantitative feedback. In some embodiments, the feedback may include qualitative feedback, such as a rating provided by requestor 303, a survey response provided by requestor 303, or other qualitative feedback. In some embodiments, the refinement of correlations of provider state models 211 to requestor state models 411, and/or the refinement of provider state models 211 and/or requestor state models 411 themselves, may be performed based on feedback in live, "real world" scenarios in addition to, or in lieu of, simulated service requests.

Figure 6:
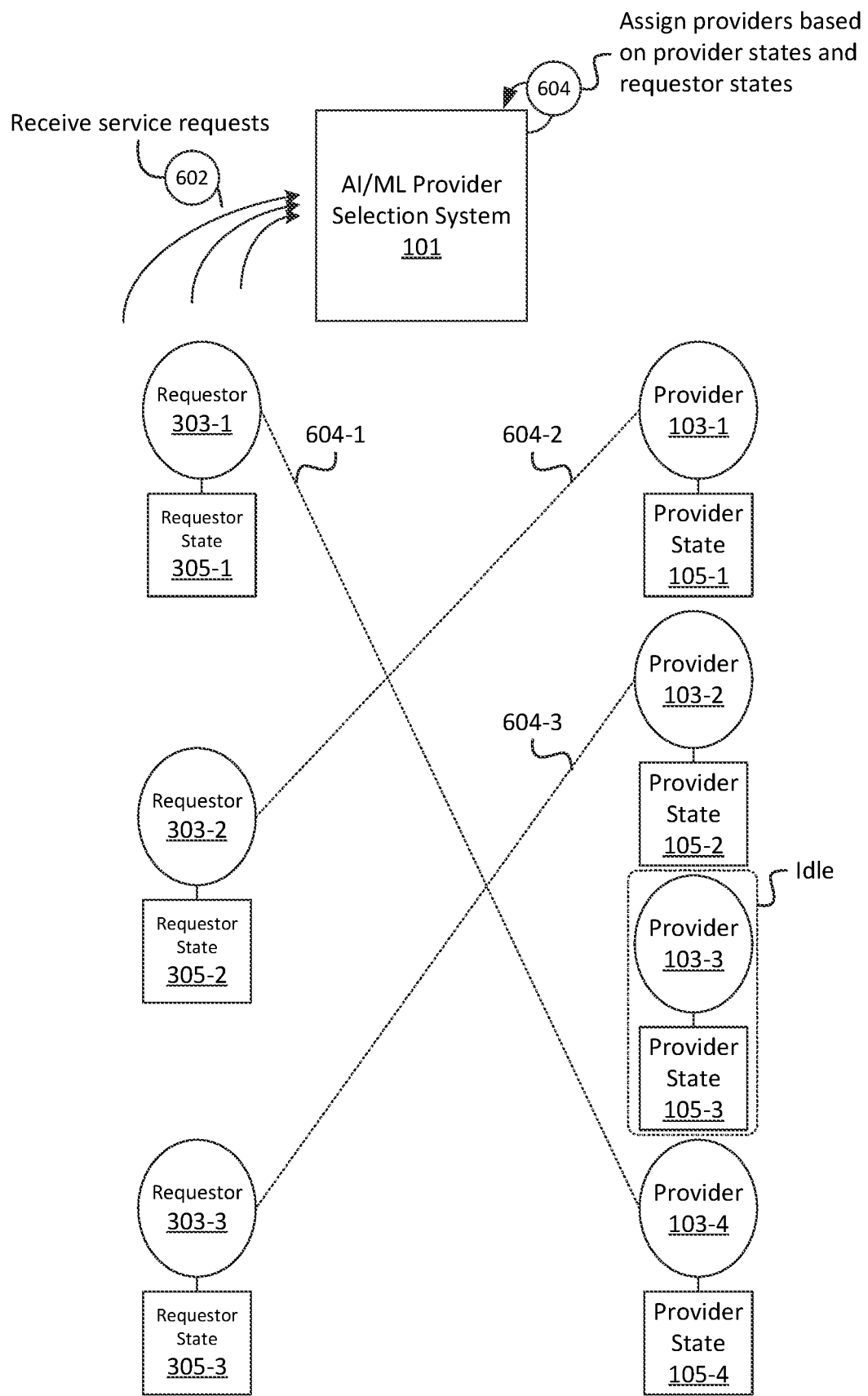
FIG. 6 illustrates an example assignment of respective providers to handle requests from a set of requestors based on provider and/or requestor models identified with respect to a set of candidate providers and the set of requestors, in accordance with some embodiments.

FIG. 6 illustrates an example selection of a set of providers 103 to provide service in response to a set of service requests from a set of requestors 303. For example, as shown, APSS 101 may receive (at 602) an indication that service requests have been received from requestor 303-1, requestor 303-2, and requestor 303-2. As similarly discussed above, APSS 101 may determine respective requestor states 305 for requestors 303, and may determine respective provider states 105 for providers 103. As also discussed above, requestor states 305 and provider states 105 may include and/or may be otherwise based on requestor state models 411 and provider state models 211, respectively.

Based on correlating requestor states 305 and provider states 105 (e.g., based on measure of correlation between requestor state models 411 and provider state models 211, as discussed above), APSS 101 may assign (at 604) respective providers 103 to provide service to requestors 303. For example, APSS 101 may assign (at 604-1) provider 103-4 to provide service in response to a request from requestor 303-1, may assign (at 604-2) provider 103-2 to provide service in response to a request from requestor 303-2, and may assign (at 604-3) provider 103-2 to provide service in response to a request from requestor 303-3.

In this example, the set of candidate providers 103 includes more providers 103 than pending requests from requestors 303. As such, fewer than all of the candidate providers 103 may be selected to handle the requests. For example, as shown, provider 103-3 may be "idle" or not assigned. Provider 103-3 may thus be available for subsequent requests (e.g., from other requestors 303). In some embodiments, APSS 101 may determine that provider 103-3 should be idle, or not assigned to handle service requests, for a particular period of time based on provider state 105-3. For example, APSS 101 may determine that provider state 105-3 is associated with a state of tiredness, frustration, or the like, and may accordingly determine that provider 103 should be idle for some time (e.g., 5 minutes, 60 minutes, 4 hours, etc.). The idle time assigned to provider 103-3 may result, for example, in the change of state from provider state 105-3 to another provider state 105 which is associated with less tiredness, frustration, etc. After such change, provider 103-3 may become more likely to be selected to handle service requests.

Figure 7:
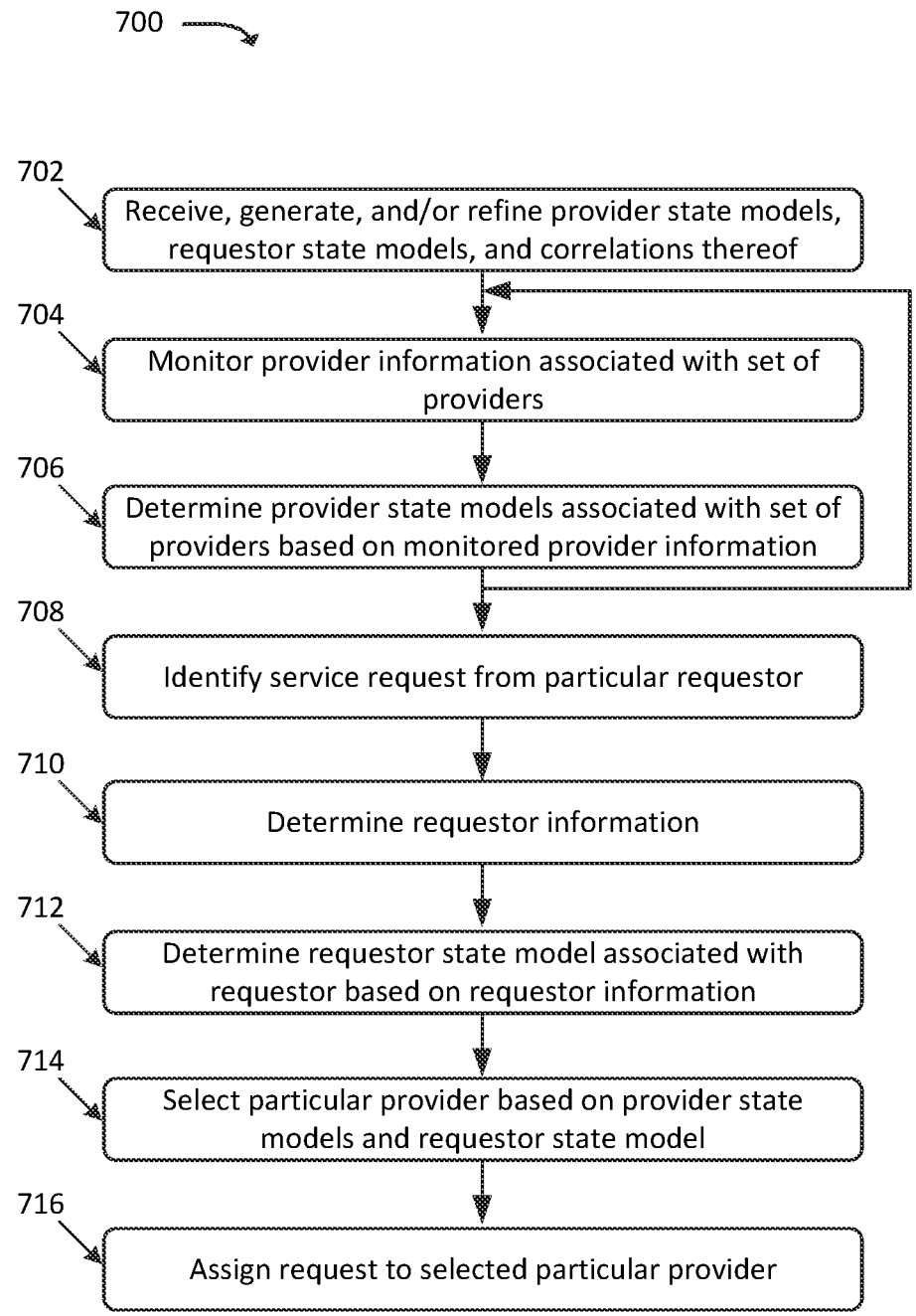
FIG. 7 illustrates an example process for assigning a provider to handle a service request from a particular requestor, in accordance with some embodiments.

FIG. 7 illustrates an example process 700 for assigning a provider 103 to handle a service request from a particular requestor 303. In some embodiments, some or all of process 700 may be performed by APSS 101. In some embodiments, one or more other devices may perform some or all of process 700 in concert with, and/or in lieu of, APSS 101.

As shown, process 700 may include receiving, generating, and/or refining (at 702) provider state models 211, requestor state models 411, and/or correlations thereof. For example, as discussed above, provider state models 211 may include brain wave information 203, speech pattern information 205, facial expression information 207, pulse and/or blood pressure information 209, and/or other suitable factors based on which the state of a given provider 103 may be determined, classified, categorized, clustered, etc. For example, a first provider state model 211 may be associated with a "happy" or "content" state, while a second provider state model 211 may be associated with a "frustrated" or "tired" state. As also discussed above, requestor state models 411 may include request type information 403, speech pattern information 405, request history information 407, and/or other suitable factors based on which the state of a given requestor 303 may be determined, classified, categorized, clustered, etc. For example, a first requestor state model 411 may be associated with an "inquisitive" state, while a second requestor state model 411 may be associated with an "angry" state.

As discussed above, APSS 101 may generate, refine, etc. correlations between particular provider state models 211 and requestor state models 411. For example, APSS 101 may utilize AI/ML techniques or other suitable techniques to determine affinities, scores, etc. that reflect a measure of correlation between a particular provider state model 211 and one or more requestor state models 411. Additionally, or alternatively, APSS 101 may utilize AI/ML techniques or other suitable techniques to determine affinities, scores, etc. that reflect a measure of correlation between a particular requestor state model 411 and one or more provider state models 211.

Process 700 may further include monitoring (at 704) provider information associated with a set of providers 103. For example, as discussed above, APSS 101 may receive biometric and/or sensor information from one or more UEs 201. UEs 201 may include and/or may be communicatively coupled to sensors or other devices or systems that are suitable to collect some or all of the provider information discussed above. For example, UEs 201 may include and/or may be communicatively coupled to an EEG device, an ECG device, a pulse monitor, a blood pressure monitor, a camera, and/or some other suitable device or system.

Process 700 may additionally include determining (at 706) provider state models 211 associated with providers 103 based on the monitored provider information. For example, as discussed above, provider state models 211 may include a set of attributes, characteristics, values, etc. that APSS 101 may match to the monitored provider information. Generally, for example, different provider state models 211 may be associated with different provider states, such as "happy," "upset," "tired," etc.

As indicated in the figure, blocks 704 and/or 706 may be repeated iteratively and/or on an ongoing basis. For example, APSS 101 may monitor (at 704) provider information on a periodic and/or intermittent basis. In some embodiments, APSS 101 may "pull" provider information by requesting or polling one or more UEs 201 or other devices or systems, and/or provider information may be "pushed" to APSS 101 (e.g., without and/or independent of requests for such information from APSS 101). In this manner, APSS 101 may maintain up-to-date, real time, and/or near-real time provider state models 211 associated with respective providers 103.

Process 700 may also include identifying (at 708) a service request from a particular requestor 303. For example, APSS 101 may receive an indication from a device or system that receives and/or handles service requests from requestors 303. For example, APSS 101 may be communicatively coupled a web portal, an interactive voice response ("IVR") system, a call center, an application server, and/or one or more other devices or systems that receive and/or otherwise handle service requests from requestors 303.

Process 700 may further include determining (at 710) requestor information associated with requestor 303. For example, as discussed above, APSS 101 may determine or receive request type information 403, speech pattern information 405, request history information 407 from one or more UEs 201 associated with requestor 303, and/or may determine such information based on information received from one or more UEs 201. For example, a particular UE 201 may provide audio data associated with requestor 303 (e.g., UE 201 may include a mobile telephone that includes a microphone that captures audible speech), and APSS 101 may analyze the audio data to determine request type information 403, speech pattern information 405, and/or other features or derivatives of the audio data.

In some embodiments, APSS 101 may determine (at 710) the requestor information in response to identifying (at 708) a service request from requestor 303. Additionally, or alternatively, APSS 101 may receive and/or determine requestor information on some other basis, which may be independent of when service requests are received from requestor 303. For example, APSS 101 may monitor information associated with requestor 303 on an ongoing basis by communicating with one or more UEs 201 or other devices or systems associated with requestor 303.

Process 700 may additionally include determining (at 712) a particular requestor state model 411 associated with requestor 303 based on the requestor information. For example, as discussed above, APSS 101 may identify a particular requestor state model 411 that includes attributes, features, characteristics, etc. that match the requestor information. As discussed above, the "matching" requestor state model 411 may include identical information as the requestor information. In some embodiments, the "matching" requestor state model 411 may include information with a measure of similarity (e.g., determined using a suitable similarity analysis) that exceeds a threshold level of similarity, and/or requestor state model 411 may have been selected from a set of candidate requestor state models 411 based on respective measures of similarity between candidate requestor state models 411 and the requestor information. For example, in some scenarios, the selected requestor state model 411 may have a highest measure of similarity to the requestor information out of the set of requestor state models 411.

Process 700 may also include selecting (at 714) a particular provider 103 based on the determined provider state model 211 and requestor state model 411. For example, as discussed above, APSS 101 may identify a particular provider 103 out of a set of candidate providers 103 to handle the service request. In some embodiments, the set of candidate providers 103 may include providers 103 that are "available" or some other suitable indicator. For example, a particular provider 103 that is currently providing service in response to a service request may not be available, while an "idle" provider 103 or provider 103 who is otherwise not currently providing service in response to a service request may be available.

As discussed above, provider 103 may be selected based on the set of provider state models 211 (determined at 706) associated with the set of candidate providers 103 and the determined (at 712) requestor state model 411 associated with requestor 303. Such selection may include identifying a particular provider state model 211 that most closely correlates to requestor state model 411 and/or one or more other factors, as mentioned above.

In some embodiments, APSS 101 may select (at 714) a particular provider 103 independent of, or without determining, requestor information or requestor state model 411. For example, APSS 101 may select a particular provider 103 based on provider state models 211. As one example, APSS 101 may determine that a first provider 103 that is associated with a "tired" state should not handle the service request, and/or may determine that a second provider 103 that is associated with a "happy" state should handle the service request.

In some embodiments, APSS 101 may generate one or more scores for each provider 103 based on the monitored (at 704) provider information, where such scores reflect the effectiveness, efficacy, or the like of providers 103. For example, APSS 101 may generate a relatively high score for a particular provider 103 whose provider information indicates (e.g., based on identifying that the provider information is associated with a particular provider state model 211) that provider 103 is alert, happy, content, and/or otherwise effective in providing services in response to service requests. On the other hand, APSS 101 may generate a relatively low score for a provider 103 whose provider information indicates (e.g., based on a particular provider state model 211 determined for provider 103) that provider 103 is tired, unhappy, frustrated, or otherwise less effective in providing services.

Process 700 may further include assigning (at 716) the request to the selected provider 103. For example, APSS 101 may output a notification to requestor 303 and/or provider 103 that provider 103 has been selected to handle the service request. In some embodiments, APSS 101 may output an instruction, notification, or other type of indication to an IVR system, web portal, application server, or other device or system. For example, APSS 101 may output an indication to a switching, routing, or selection of a call center that a particular call center representative has been selected to answer a call from a particular caller who is requesting a service such as an information request, technical support, or the like. Since the selection of the call representative may be based on the state of the representative (e.g., happy, attentive, tired, etc.) and/or the caller (e.g., surprised, upset, inquisitive, etc.), the subsequent interactions between the representative and the caller may have a higher likelihood of being expedient, convenient, or otherwise positive than if the states of the representative and/or the caller were not a factor in the selection.

While examples are provided above in the context of matching a given request or associated requestor 303 to a particular provider 103 (e.g., based on provider states and/or requestor states), similar concepts may apply to embodiments that are independent of requests or requestors 303, and/or in which no such requests or requestors 303 exist. For example, APSS 101 may determine (at 706) a provider state model 211 associated with a particular provider 103, and may determine one or more actions (e.g., remedial actions or other types of actions) based on the determined provider state model 211. For example, APSS 101 may generate, maintain, refine, etc. (e.g., using AI/ML techniques or other suitable techniques) associations between particular provider state models 211 and associated actions. As one example, a given provider state model 211 may indicate an "overworked" or "tired" state for provider 103, and may be associated with an action that includes notifying provider 103 to take a break for a given amount of time.

Similarly, different provider state models 211, associated with different attributes or characteristics (e.g., different biometric and/or other types of information) of provider 103 may be associated with different actions, or different parameters for the same action. For example, one provider state model 211 may be associated with a first set of provider information (e.g., biometrics and/or other suitable information), and may be associated with an action including notifying provider 103 to take a break for a first period of time (e.g., one hour), while another provider state model 211 may be associated with a second set of provider information (e.g., different biometrics or different values for the biometrics than the first set of provider information) and may be associated with an action notifying provider 103 to take a break for a second period of time (e.g., two hours).

In some embodiments, the actions or remedial actions may include generating one or more reports reflecting the state of one or more providers 103 over time. Such reports may include graphs, charts, tables, or the like. For example, such reports may include a "happiness over time" graph, a "tiredness over time" graph, or the like, where such reports are generated based on provider state models 211 determined for providers 103 over time. In some embodiments, the reports may be generated for a single provider 103 or a group of providers 103. In this manner, the states of individuals or groups (e.g., departments, divisions, etc. of an organization) may be readily determined and analyzed.

In some embodiments, the remedial action may include reassigning a given provider 103 to a different department, category, queue, etc. For example, a first department to which provider 103 is assigned may handle a first category of requests (e.g., technical support requests), while a second department may handle a second category of requests (e.g., general information requests). APSS 101 may have determined that the first department and the second department are associated with respective providers with respective provider states 211, and may determine that the second department is a better fit for particular provider 103. For example, APSS 101 may determine that provider 103 is in a "stressed" state, and may determine that providers associated with the second department are less likely to be associated with the "stressed" state than providers of the first department. In such a scenario, APSS 101 may output an indication that provider 103 should be reassigned to the second department. Such reassignment may cause the state of provider 103 to change over time (e.g., to a state other than a "stressed" state).

Figure 8:
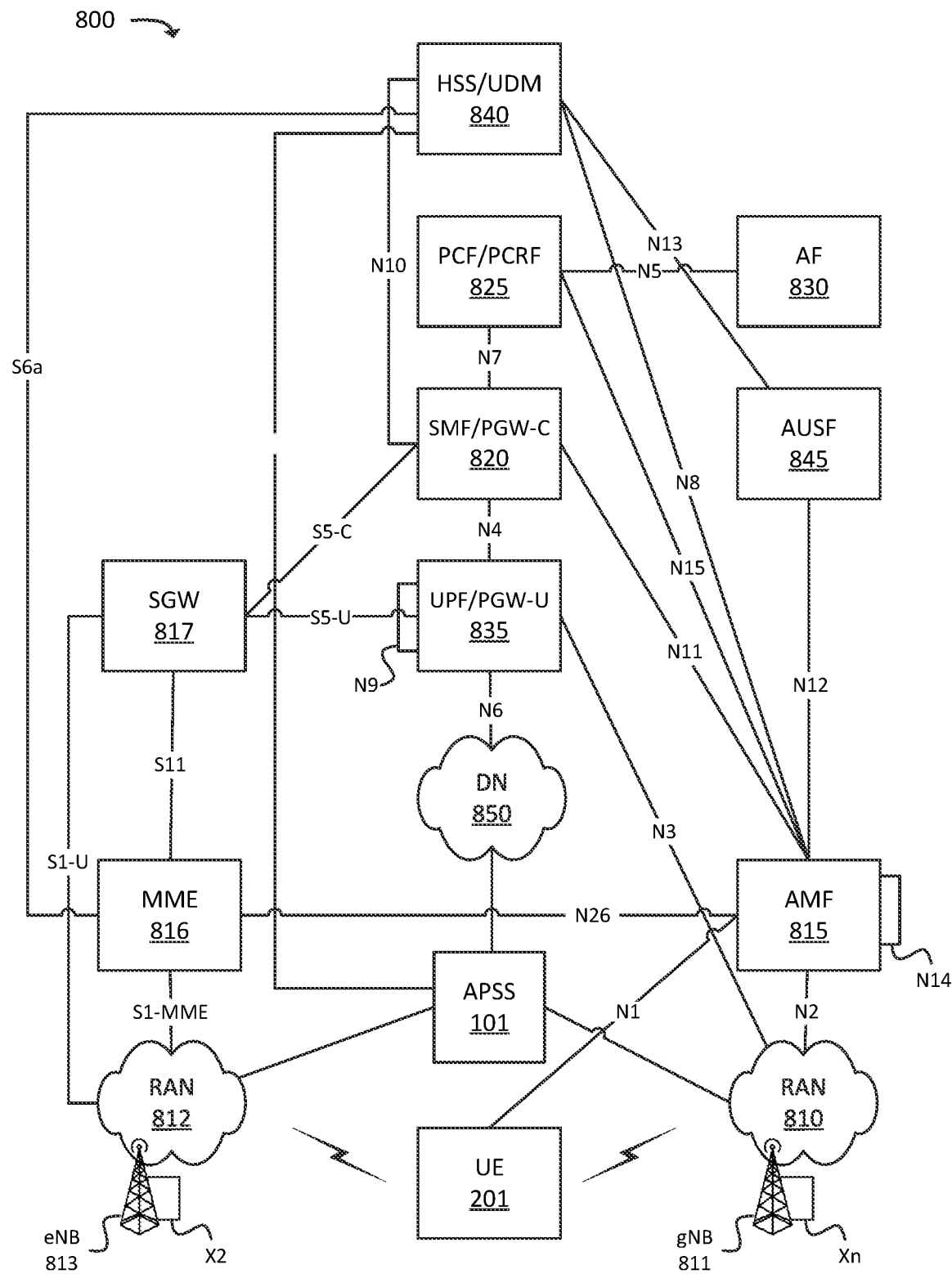
FIG. 8 illustrates an example environment in which one or more embodiments, described herein, may be implemented.

FIG. 8 illustrates an example environment 800, in which one or more embodiments may be implemented. In some embodiments, environment 800 may correspond to a Fifth Generation ("5G") network, and/or may include elements of a 5G network. In some embodiments, environment 800 may correspond to a 5G Non-Standalone ("NSA") architecture, in which a 5G radio access technology ("RAT") may be used in conjunction with one or more other RATs (e.g., a Long-Term Evolution ("LTE") RAT), and/or in which elements of a 5G core network may be implemented by, may be communicatively coupled with, and/or may include elements of another type of core network (e.g., an evolved packet core ("EPC")). As shown, environment 800 may include UE 201, RAN 810 (which may include one or more Next Generation Node Bs ("gNBs") 811), RAN 812 (which may include one or more one or more evolved Node Bs ("eNBs") 813), and various network functions such as Access and Mobility Management Function ("AMF") 815, Mobility Management Entity ("MME") 816, Serving Gateway ("SGW") 817, Session Management Function ("SMF")/Packet Data Network ("PDN") Gateway ("PGW")-Control plane function ("PGW-C") 820, Policy Control Function ("PCF")/Policy Charging and Rules Function ("PCRF") 825, Application Function ("AF") 830, User Plane Function ("UPF")/PGW-User plane function ("PGW-U") 835, Home Subscriber Server ("HSS")/Unified Data Management ("UDM") 840, and Authentication Server Function ("AUSF") 845. Environment 800 may also include one or more networks, such as Data Network ("DN") 850. Environment 800 may include one or more additional devices or systems communicatively coupled to one or more networks (e.g., DN 850), such as APSS 101.

The example shown in FIG. 8 illustrates one instance of each network component or function (e.g., one instance of SMF/PGW-C 820, PCF/PCRF 825, UPF/PGW-U 835, HSS/UDM 840, and/or 845). In practice, environment 800 may include multiple instances of such components or functions. For example, in some embodiments, environment 800 may include multiple "slices" of a core network, where each slice includes a discrete set of network functions (e.g., one slice may include a first instance of SMF/PGW-C 820, PCF/PCRF 825, UPF/PGW-U 835, HSS/UDM 840, and/or 845, while another slice may include a second instance of SMF/PGW-C 820, PCF/PCRF 825, UPF/PGW-U 835, HSS/UDM 840, and/or 845). The different slices may provide differentiated levels of service, such as service in accordance with different Quality of Service ("QoS") parameters.

The quantity of devices and/or networks, illustrated in FIG. 8, is provided for explanatory purposes only. In practice, environment 800 may include additional devices and/or networks, fewer devices and/or networks, different devices and/or networks, or differently arranged devices and/or networks than illustrated in FIG. 8. For example, while not shown, environment 800 may include devices that facilitate or enable communication between various components shown in environment 800, such as routers, modems, gateways, switches, hubs, etc. Alternatively, or additionally, one or more of the devices of environment 800 may perform one or more network functions described as being performed by another one or more of the devices of environment 800. Devices of environment 800 may interconnect with each other and/or other devices via wired connections, wireless connections, or a combination of wired and wireless connections. In some implementations, one or more devices of environment 800 may be physically integrated in, and/or may be physically attached to, one or more other devices of environment 800.

UE 201 may include a computation and communication device, such as a wireless mobile communication device that is capable of communicating with RAN 810, RAN 812, and/or DN 850. UE 201 may be, or may include, a radiotelephone, a personal communications system ("PCS") terminal (e.g., a device that combines a cellular radiotelephone with data processing and data communications capabilities), a personal digital assistant ("PDA") (e.g., a device that may include a radiotelephone, a pager, Internet/intranet access, etc.), a smart phone, a laptop computer, a tablet computer, a camera, a personal gaming system, an IoT device (e.g., a sensor, a smart home appliance, or the like), a wearable device, an IoT device, a Mobile-to-Mobile ("M2M") device, or another type of mobile computation and communication device. UE 201 may send traffic to and/or receive traffic (e.g., user plane traffic) from DN 850 via RAN 810, RAN 812, and/or UPF/PGW-U 835.

RAN 810 may be, or may include, a 5G RAN that includes one or more base stations (e.g., one or more gNBs 811), via which UE 201 may communicate with one or more other elements of environment 800. UE 201 may communicate with RAN 810 via an air interface (e.g., as provided by gNB 811). For instance, RAN 810 may receive traffic (e.g., voice call traffic, data traffic, messaging traffic, signaling traffic, etc.) from UE 201 via the air interface, and may communicate the traffic to UPF/PGW-U 835, and/or one or more other devices or networks. Similarly, RAN 810 may receive traffic intended for UE 201 (e.g., from UPF/PGW-U 835, AMF 815, and/or one or more other devices or networks) and may communicate the traffic to UE 201 via the air interface.

RAN 812 may be, or may include, a LTE RAN that includes one or more base stations (e.g., one or more eNBs 813), via which UE 201 may communicate with one or more other elements of environment 800. UE 201 may communicate with RAN 812 via an air interface (e.g., as provided by eNB 813). For instance, RAN 810 may receive traffic (e.g., voice call traffic, data traffic, messaging traffic, signaling traffic, etc.) from UE 201 via the air interface, and may communicate the traffic to UPF/PGW-U 835, and/or one or more other devices or networks. Similarly, RAN 810 may receive traffic intended for UE 201 (e.g., from UPF/PGW-U 835, SGW 817, and/or one or more other devices or networks) and may communicate the traffic to UE 201 via the air interface.

AMF 815 may include one or more devices, systems, Virtualized Network Functions ("VNFs"), etc., that perform operations to register UE 201 with the 5G network, to establish bearer channels associated with a session with UE 201, to hand off UE 201 from the 5G network to another network, to hand off UE 201 from the other network to the 5G network, manage mobility of UE 201 between RANs 810 and/or gNBs 811, and/or to perform other operations. In some embodiments, the 5G network may include multiple AMFs 815, which communicate with each other via the N14 interface (denoted in FIG. 8 by the line marked "N14" originating and terminating at AMF 815).

MME 816 may include one or more devices, systems, VNFs, etc., that perform operations to register UE 201 with the EPC, to establish bearer channels associated with a session with UE 201, to hand off UE 201 from the EPC to another network, to hand off UE 201 from another network to the EPC, manage mobility of UE 201 between RANs 812 and/or eNBs 813, and/or to perform other operations.

SGW 817 may include one or more devices, systems, VNFs, etc., that aggregate traffic received from one or more eNBs 813 and send the aggregated traffic to an external network or device via UPF/PGW-U 835. Additionally, SGW 817 may aggregate traffic received from one or more UPF/PGW-Us 835 and may send the aggregated traffic to one or more eNBs 813. SGW 817 may operate as an anchor for the user plane during inter-eNB handovers and as an anchor for mobility between different telecommunication networks or RANs (e.g., RANs 810 and 812).

SMF/PGW-C 820 may include one or more devices, systems, VNFs, etc., that gather, process, store, and/or provide information in a manner described herein. SMF/PGW-C 820 may, for example, facilitate in the establishment of communication sessions on behalf of UE 201. In some embodiments, the establishment of communications sessions may be performed in accordance with one or more policies provided by PCF/PCRF 825.

PCF/PCRF 825 may include one or more devices, systems, VNFs, etc., that aggregate information to and from the 5G network and/or other sources. PCF/PCRF 825 may receive information regarding policies and/or subscriptions from one or more sources, such as subscriber databases and/or from one or more users (such as, for example, an administrator associated with PCF/PCRF 825).

AF 830 may include one or more devices, systems, VNFs, etc., that receive, store, and/or provide information that may be used in determining parameters (e.g., quality of service parameters, charging parameters, or the like) for certain applications.

UPF/PGW-U 835 may include one or more devices, systems, VNFs, etc., that receive, store, and/or provide data (e.g., user plane data). For example, UPF/PGW-U 835 may receive user plane data (e.g., voice call traffic, data traffic, etc.), destined for UE 201, from DN 850, and may forward the user plane data toward UE 201 (e.g., via RAN 810, SMF/PGW-C 820, and/or one or more other devices). In some embodiments, multiple UPFs 835 may be deployed (e.g., in different geographical locations), and the delivery of content to UE 201 may be coordinated via the N9 interface (e.g., as denoted in FIG. 8 by the line marked "N9" originating and terminating at UPF/PGW-U 835). Similarly, UPF/PGW-U 835 may receive traffic from UE 201 (e.g., via RAN 810, SMF/PGW-C 820, and/or one or more other devices), and may forward the traffic toward DN 850. In some embodiments, UPF/PGW-U 835 may communicate (e.g., via the N4 interface) with SMF/PGW-C 820, regarding user plane data processed by UPF/PGW-U 835.

HSS/UDM 840 and AUSF 845 may include one or more devices, systems, VNFs, etc., that manage, update, and/or store, in one or more memory devices associated with AUSF 845 and/or HSS/UDM 840, profile information associated with a subscriber. AUSF 845 and/or HSS/UDM 840 may perform authentication, authorization, and/or accounting operations associated with the subscriber and/or a communication session with UE 201.

DN 850 may include one or more wired and/or wireless networks. For example, DN 850 may include an Internet Protocol ("IP")-based PDN, a wide area network ("WAN") such as the Internet, a private enterprise network, and/or one or more other networks. UE 201 may communicate, through DN 850, with data servers, other UEs 201, and/or to other servers or applications that are coupled to DN 850. DN 850 may be connected to one or more other networks, such as a public switched telephone network ("PSTN"), a public land mobile network ("PLMN"), and/or another network. DN 850 may be connected to one or more devices, such as content providers, applications, web servers, and/or other devices, with which UE 201 may communicate.

APSS 101 may include one or more devices, systems, VNFs, etc. that perform one or more of the operations discussed herein. For example, APSS 101 may receive, generate, and/or refine one or more provider state models 211, requestor state models 411, and/or correlations thereof. APSS 101 may monitor and/or otherwise determine information associated with one or more providers 103 and/or requestor 303. For example, APSS 101 may receive such information from one or more UEs 201 and/or other devices or systems that determine, collect, receive, etc. such information. APSS 101 may select a particular provider 103 to respond to a service request from a given requestor 303 based on provider state models 211, requestor state models 411, correlations thereof, and/or other suitable information. APSS 101 may output an indication of the selection to one or more UEs 201 or other devices or systems that are communicatively coupled to one or more UEs 201 associated with provider 103 and/or requestor 303.

Figure 9:
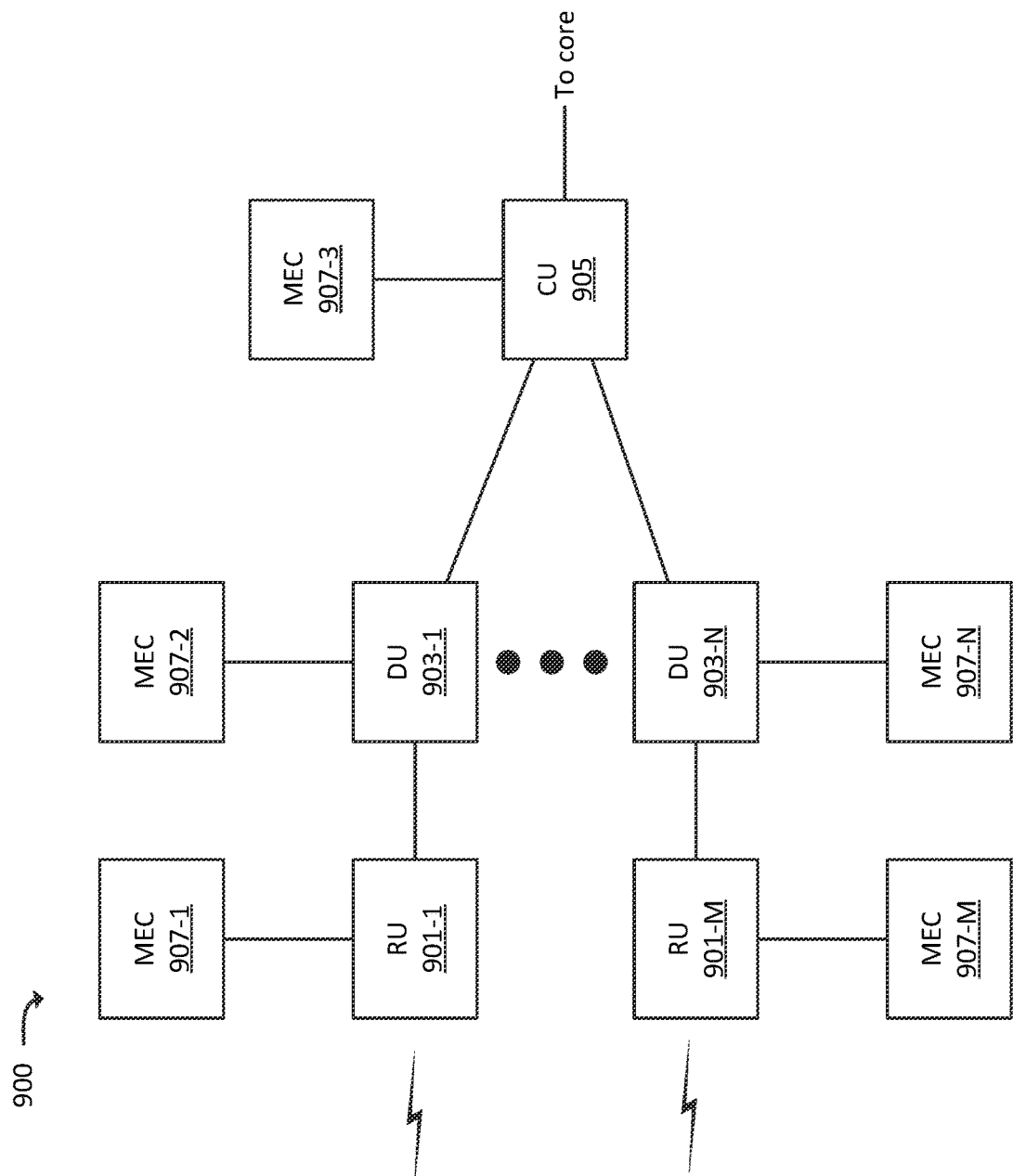
FIG. 9 illustrates an example arrangement of a radio access network ("RAN"), in accordance with some embodiments.

FIG. 9 illustrates an example Distributed Unit ("DU") network 900, which may be included in and/or implemented by one or more RANs (e.g., RAN 810, RAN 812, or some other RAN). In some embodiments, a particular RAN may include one DU network 900. In some embodiments, a particular RAN may include multiple DU networks 900. In some embodiments, DU network 900 may correspond to a particular gNB 811 of a 5G RAN (e.g., RAN 810). In some embodiments, DU network 900 may correspond to multiple gNBs 811. In some embodiments, DU network 900 may correspond to one or more other types of base stations of one or more other types of RANs. As shown, DU network 900 may include Central Unit ("CU") 905, one or more Distributed Units ("DUs") 903-1 through 903-N (referred to individually as "DU 903," or collectively as "DUs 903"), and one or more Radio Units ("RUs") 901-1 through 901-M (referred to individually as "RU 901," or collectively as "RUs 901").

CU 905 may communicate with a core of a wireless network (e.g., may communicate with one or more of the devices or systems described above with respect to FIG. 8, such as AMF 815 and/or UPF/PGW-U 835). In the uplink direction (e.g., for traffic from UEs 201 to a core network), CU 905 may aggregate traffic from DUs 903, and forward the aggregated traffic to the core network. In some embodiments, CU 905 may receive traffic according to a given protocol (e.g., Radio Link Control ("RLC")) from DUs 903, and may perform higher-layer processing (e.g., may aggregate/process RLC packets and generate Packet Data Convergence Protocol ("PDCP") packets based on the RLC packets) on the traffic received from DUs 903.

In accordance with some embodiments, CU 905 may receive downlink traffic (e.g., traffic from the core network) for a particular UE 201, and may determine which DU(s) 903 should receive the downlink traffic. DU 903 may include one or more devices that transmit traffic between a core network (e.g., via CU 905) and UE 201 (e.g., via a respective RU 901). DU 903 may, for example, receive traffic from RU 901 at a first layer (e.g., physical ("PHY") layer traffic, or lower PHY layer traffic), and may process/aggregate the traffic to a second layer (e.g., upper PHY and/or RLC). DU 903 may receive traffic from CU 905 at the second layer, may process the traffic to the first layer, and provide the processed traffic to a respective RU 901 for transmission to UE 201.

RU 901 may include hardware circuitry (e.g., one or more RF transceivers, antennas, radios, and/or other suitable hardware) to communicate wirelessly (e.g., via an RF interface) with one or more UEs 201, one or more other DUs 903 (e.g., via RUs 901 associated with DUs 903), and/or any other suitable type of device. In the uplink direction, RU 901 may receive traffic from UE 201 and/or another DU 903 via the RF interface and may provide the traffic to DU 903. In the downlink direction, RU 901 may receive traffic from DU 903, and may provide the traffic to UE 201 and/or another DU 903.

RUs 901 may, in some embodiments, be communicatively coupled to one or more Multi-Access/Mobile Edge Computing ("MEC") devices, referred to sometimes herein simply as ("MECs") 907. For example, RU 901-1 may be communicatively coupled to MEC 907-1, RU 901-M may be communicatively coupled to MEC 907-M, DU 903-1 may be communicatively coupled to MEC 907-2, DU 903-N may be communicatively coupled to MEC 907-N, CU 905 may be communicatively coupled to MEC 907-3, and so on. MECs 907 may include hardware resources (e.g., configurable or provisionable hardware resources) that may be configured to provide services and/or otherwise process traffic to and/or from UE 201, via a respective RU 901.

For example, RU 901-1 may route some traffic, from UE 201, to MEC 907-1 instead of to a core network (e.g., via DU 903 and CU 905). MEC 907-1 may process the traffic, perform one or more computations based on the received traffic, and may provide traffic to UE 201 via RU 901-1. In this manner, ultra-low latency services may be provided to UE 201, as traffic does not need to traverse DU 903, CU 905, and an intervening backhaul network between DU network 900 and the core network. In some embodiments, MEC 907 may include, and/or may implement some or all of the functionality described above with respect to APSS 101.

FIG. 10 illustrates example components of device 1000. One or more of the devices described above may include one or more devices 1000. Device 1000 may include bus 1010, processor 1020, memory 1030, input component 1040, output component 1050, and communication interface 1060. In another implementation, device 1000 may include additional, fewer, different, or differently arranged components.

Bus 1010 may include one or more communication paths that permit communication among the components of device 1000. Processor 1020 may include a processor, microprocessor, or processing logic that may interpret and execute instructions. Memory 1030 may include any type of dynamic storage device that may store information and instructions for execution by processor 1020, and/or any type of non-volatile storage device that may store information for use by processor 1020.

Input component 1040 may include a mechanism that permits an operator to input information to device 1000 and/or other receives or detects input from a source external to 1040, such as a touchpad, a touchscreen, a keyboard, a keypad, a button, a switch, a microphone or other audio input component, etc. In some embodiments, input component 1040 may include, or may be communicatively coupled to, one or more sensors, such as a motion sensor (e.g., which may be or may include a gyroscope, accelerometer, or the like), a location sensor (e.g., a Global Positioning System ("GPS")-based location sensor or some other suitable type of location sensor or location determination component), a thermometer, a barometer, a biometric sensor (e.g., a fingerprint sensor, an EEG monitor, an ECG monitor, a blood pressure sensor, a pulse and/or heartbeat sensor, or the like), and/or some other type of sensor. Output component 1050 may include a mechanism that outputs information to the operator, such as a display, a speaker, one or more light emitting diodes ("LEDs"), etc.

Communication interface 1060 may include any transceiver-like mechanism that enables device 1000 to communicate with other devices and/or systems. For example, communication interface 1060 may include an Ethernet interface, an optical interface, a coaxial interface, or the like. Communication interface 1060 may include a wireless communication device, such as an infrared ("IR") receiver, a Bluetooth® radio, or the like. The wireless communication device may be coupled to an external device, such as a remote control, a wireless keyboard, a mobile telephone, etc. In some embodiments, device 1000 may include more than one communication interface 1060. For instance, device 1000 may include an optical interface and an Ethernet interface.

Device 1000 may perform certain operations relating to one or more processes described above. Device 1000 may perform these operations in response to processor 1020 executing software instructions stored in a computer-readable medium, such as memory 1030. A computer-readable medium may be defined as a non-transitory memory device. A memory device may include space within a single physical memory device or spread across multiple physical memory devices. The software instructions may be read into memory 1030 from another computer-readable medium or from another device. The software instructions stored in memory 1030 may cause processor 1020 to perform processes described herein. Alternatively, hardwired circuitry may be used in place of or in combination with software instructions to implement processes described herein. Thus, implementations described herein are not limited to any specific combination of hardware circuitry and software.

The foregoing description of implementations provides illustration and description, but is not intended to be exhaustive or to limit the possible implementations to the precise form disclosed. Modifications and variations are possible in light of the above disclosure or may be acquired from practice of the implementations.

For example, while series of blocks and/or signals have been described above (e.g., with regard to FIGS. 1-7), the order of the blocks and/or signals may be modified in other implementations. Further, non-dependent blocks and/or signals may be performed in parallel. Additionally, while the figures have been described in the context of particular devices performing particular acts, in practice, one or more other devices may perform some or all of these acts in lieu of, or in addition to, the above-mentioned devices.

The actual software code or specialized control hardware used to implement an embodiment is not limiting of the embodiment. Thus, the operation and behavior of the embodiment has been described without reference to the specific software code, it being understood that software and control hardware may be designed based on the description herein.

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

Further, while certain connections or devices are shown, in practice, additional, fewer, or different, connections or devices may be used. Furthermore, while various devices and networks are shown separately, in practice, the functionality of multiple devices may be performed by a single device, or the functionality of one device may be performed by multiple devices. Further, multiple ones of the illustrated networks may be included in a single network, or a particular network may include multiple networks. Further, while some devices are shown as communicating with a network, some such devices may be incorporated, in whole or in part, as a part of the network.

To the extent the aforementioned implementations collect, store, or employ personal information of individuals, groups or other entities, it should be understood that such information shall be used in accordance with all applicable laws concerning protection of personal information. Additionally, the collection, storage, and use of such information can be subject to consent of the individual to such activity, for example, through well known "opt-in" or "opt-out" processes as can be appropriate for the situation and type of information. Storage and use of personal information can be in an appropriately secure manner reflective of the type of information, for example, through various access control, encryption and anonymization techniques for particularly sensitive information.

No element, act, or instruction used in the present application should be construed as critical or essential unless explicitly described as such. An instance of the use of the term "and," as used herein, does not necessarily preclude the interpretation that the phrase "and/or" was intended in that instance. Similarly, an instance of the use of the term "or," as used herein, does not necessarily preclude the interpretation that the phrase "and/or" was intended in that instance. Also, as used herein, the article "a" is intended to include one or more items, and may be used interchangeably with the phrase "one or more." Where only one item is intended, the terms "one," "single," "only," or similar language is used. Further, the phrase "based on" is intended to mean "based, at least in part, on" unless explicitly stated otherwise.

What is claimed is:

1. A device, comprising:
one or more processors configured to:
maintain a first set of artificial intelligence/machine learning ("AI/ML") models that correlate respective sets of brain wave information to respective provider states;
measure brain wave information associated with a plurality of service providers via one or more Electroencephalography ("EEG") devices;
determine a particular provider state associated with each respective service provider, of the plurality of service providers, based on the measured brain wave information associated with each respective service provider, wherein determining the provider state for each service provider includes:
comparing the measured brain wave information, associated with each service provider, to the first set of AI/ML models,
identifying, for each service provider and based on the comparing, a respective AI/ML model that corresponds to the respective brain wave information associated with the each service provider, and
identifying a particular provider state, for each service provider, based on the identified AI/ML model for the each service provider;
maintain a plurality of service queues that are each associated with a respective type of service request;
maintain a second set of AI/ML models that correlate respective provider states to respective service queues of the plurality of service queues;
assign particular service providers to respective service queues, of the plurality of service queues, based on comparing respective provider states of the plurality of providers to the second set of AI/ML models;

receive an indication of a service request;
identify a particular type of the service request;
select, based on the determined provider states, a particular service provider, of the plurality of service providers, to respond to the service request, wherein selecting the particular service provider includes:
  selecting a particular service queue, out of the plurality of service queues, that are associated with the particular type of the service request, and
  selecting the particular service provider from the service providers assigned to the particular service queue; and
respond to the service request by providing an indication of the selected particular service provider.

2. The device of claim 1, wherein selecting the particular service provider includes generating a score for each service provider, of the plurality of service providers, wherein the generated scores are based on respective biometric information associated with each service provider.

3. The device of claim 1, wherein the one or more processors are further configured to:
  determine a particular requestor state associated with the service request; and
  determine a respective measure of correlation between each provider state, of the determined provider states, and the particular requestor state,
  wherein selecting the particular service provider is based on the determined respective measures of correlation between the determined provider states and the particular requestor state.

4. The device of claim 1, wherein determining the particular provider state associated with each particular service provider, of the plurality of service providers, further includes at least one of:
  determining speech pattern information associated with the one or more service providers,
  determining pulse information associated with the one or more service providers, or
  determining blood pressure information associated with the one or more service providers.

5. The device of claim 1, wherein the particular service provider is a first service provider, wherein the one or more processors are further configured to:
  identify that a second service provider, of the plurality of service providers, is associated with a particular provider state; and
  output an alert that the particular service provider is associated with the particular provider state.

6. The device of claim 1, wherein the particular service provider is a first service provider, wherein the one or more processors are further configured to:
  identify that a second service provider, of the plurality of service providers, is associated with a particular provider state; and
  reassign, based on identifying that the second service provider is associated with the particular provider state, from a first service queue associated with a first type of service request to a second queue associated with a second type of service request.

7. The device of claim 1,
wherein determining the particular provider state associated with each respective service provider, of the plurality of service providers, includes:
  monitoring first biometric information associated with a first service provider of the plurality of service providers over a first period of time, and
  monitoring second biometric information associated with the first service provider over a second period of time that is subsequent to the first period of time;
wherein the one or more processors are further configured to:
  determine that the second biometric information differs from the first biometric information; and
  update, based on determining that the second biometric information differs from the first biometric information, provider state information associated with the first service provider from a first provider state, associated with the first period of time, to a second provider state, associated with the second period of time.

8. A non-transitory computer-readable medium, storing a plurality of processor-executable instructions to:
  maintain a first set of artificial intelligence/machine learning ("AI/ML") models that correlate respective sets of brain wave information to respective provider states;
  measure brain wave information associated with a plurality of service providers via one or more Electroencephalography ("EEG") devices;
  determine a particular provider state associated with each respective service provider, of the plurality of service providers, based on the measured brain wave information associated with each respective service provider, wherein determining the provider state for each service provider includes:
    comparing the measured brain wave information, associated with each service provider, to the first set of AI/ML models,
    identifying, for each service provider and based on the comparing, a respective AI/ML model that corresponds to the respective brain wave information associated with the each service provider, and
    identifying a particular provider state, for each service provider, based on the identified AI/ML model for the each service provider;
  maintain a plurality of service queues that are each associated with a respective type of service request;
  maintain a second set of AI/ML models that correlate respective provider states to respective service queues of the plurality of service queues;
  assign particular service providers to respective service queues, of the plurality of service queues, based on comparing respective provider states of the plurality of providers to the second set of AI/ML models;
  receive an indication of a service request;
  identify a particular type of the service request;
  select, based on the determined provider states, a particular service provider, of the plurality of service providers, to respond to the service request, wherein selecting the particular service provider includes:
    selecting a particular service queue, out of the plurality of service queues, that are associated with the particular type of the service request, and
    selecting the particular service provider from the service providers assigned to the particular service queue; and
  respond to the service request by providing an indication of the selected particular service provider.

9. The non-transitory computer-readable medium of claim 8, wherein selecting the particular service provider includes generating a score for each service provider, of the plurality of service providers, wherein the generated scores are based on respective biometric information associated with each service provider.

10. The non-transitory computer-readable medium of claim 8, wherein the plurality of processor-executable instructions further include processor-executable instructions to:
  determine a particular requestor state associated with the service request; and
  determine a respective measure of correlation between each provider state, of the determined provider states, and the particular requestor state,
  wherein selecting the particular service provider is based on the determined respective measures of correlation between the determined provider states and the particular requestor state.

11. The non-transitory computer-readable medium of claim 8, wherein determining the particular provider state associated with each particular service provider, of the plurality of service providers, further includes at least one of:
  determining speech pattern information associated with the one or more service providers,
  determining pulse information associated with the one or more service providers, or
  determining blood pressure information associated with the one or more service providers.

12. The non-transitory computer-readable medium of claim 8, wherein the particular service provider is a first service provider, wherein the plurality of processor-executable instructions further include processor-executable instructions to:
  identify that a second service provider, of the plurality of service providers, is associated with a particular provider state; and
  output an alert that the particular service provider is associated with the particular provider state.

13. The non-transitory computer-readable medium of claim 8, wherein the particular service provider is a first service provider, wherein the plurality of processor-executable instructions further include processor-executable instructions to:
  identify that a second service provider, of the plurality of service providers, is associated with a particular provider state; and
  reassign, based on identifying that the second service provider is associated with the particular provider state, from a first service queue associated with a first type of service request to a second queue associated with a second type of service request.

14. The non-transitory computer-readable medium of claim 8,
  wherein determining the particular provider state associated with each respective service provider, of the plurality of service providers, includes:
    monitoring first biometric information associated with a first service provider of the plurality of service providers over a first period of time, and
    monitoring second biometric information associated with the first service provider over a second period of time that is subsequent to the first period of time;
  wherein the plurality of processor-executable instructions further include processor-executable instructions to:
    determine that the second biometric information differs from the first biometric information; and
    update, based on determining that the second biometric information differs from the first biometric information, provider state information associated with the first service provider from a first provider state, associated with the first period of time, to a second provider state, associated with the second period of time.

15. A method, comprising:
  maintaining a first set of artificial intelligence/machine learning ("AI/ML") models that correlate respective sets of brain wave information to respective provider states;
  measuring brain wave information associated with a plurality of service providers via one or more Electroencephalography ("EEG") devices;
  determining a particular provider state associated with each respective service provider, of the plurality of service providers, based on the measured brain wave information associated with each respective service provider, wherein determining the provider state for each service provider includes:
    comparing the measured brain wave information, associated with each service provider, to the first set of AI/ML models,
    identifying, for each service provider and based on the comparing, a respective AI/ML model that corresponds to the respective brain wave information associated with the each service provider, and
    identifying a particular provider state, for each service provider, based on the identified AI/ML model for the each service provider;
  maintaining a plurality of service queues that are each associated with a respective type of service request;
  maintaining a second set of AI/ML models that correlate respective provider states to respective service queues of the plurality of service queues;
  assigning particular service providers to respective service queues, of the plurality of service queues, based on comparing respective provider states of the plurality of providers to the second set of AI/ML models;
  receiving an indication of a service request;
  identifying a particular type of the service request;
  selecting, based on the determined provider states, a particular service provider, of the plurality of service providers, to respond to the service request, wherein selecting the particular service provider includes:
    selecting a particular service queue, out of the plurality of service queues, that are associated with the particular type of the service request, and
    selecting the particular service provider from the service providers assigned to the particular service queue; and
  responding to the service request by providing an indication of the selected particular service provider.

16. The method of claim 15, wherein selecting the particular service provider includes generating a score for each service provider, of the plurality of service providers, wherein the generated scores are based on respective biometric information associated with each service provider.

17. The method of claim 15, the method further comprising:
  determining a particular requestor state associated with the service request; and
  determining a respective measure of correlation between each provider state, of the determined provider states, and the particular requestor state,
  wherein selecting the particular service provider is based on the determined respective measures of correlation between the determined provider states and the particular requestor state.

18. The method of claim 15, wherein determining the particular provider state associated with each particular service provider, of the plurality of service providers, further includes at least one of:
- determining speech pattern information associated with the one or more service providers,
- determining pulse information associated with the one or more service providers, or
- determining blood pressure information associated with the one or more service providers.

19. The method of claim 15, wherein the particular service provider is a first service provider, the method further comprising:
- identifying that a second service provider, of the plurality of service providers, is associated with a particular provider state; and
- outputting an alert that the particular service provider is associated with the particular provider state.

20. The method of claim 15, wherein the particular service provider is a first service provider, the method further comprising:
- identifying that a second service provider, of the plurality of service providers, is associated with a particular provider state; and
- reassigning, based on identifying that the second service provider is associated with the particular provider state, from a first service queue associated with a first type of service request to a second queue associated with a second type of service request.

* * * * *